(12) United States Patent
Takeda et al.

(10) Patent No.: US 9,981,905 B2
(45) Date of Patent: May 29, 2018

(54) AROMATIC DIAMINE, AN INTERMEDIATE THEREFOR, A METHOD FOR PRODUCING THE AROMATIC DIAMINE, AND A METHOD FOR PRODUCING THE INTERMEDIATE THEREFOR

(71) Applicant: SEIKA CORPORATION, Wakayama, Wakayama (JP)

(72) Inventors: Motonori Takeda, Wakayama (JP); Masahiro Kasamatsu, Wakayama (JP); Akihiro Tamaki, Wakayama (JP)

(73) Assignee: SEIKA CORPORATION, Wakayama (JP)

( * ) Notice: Subject to any disclaimer, the term of this patent is extended or adjusted under 35 U.S.C. 154(b) by 0 days. days.

(21) Appl. No.: 15/565,658

(22) PCT Filed: Dec. 14, 2015

(86) PCT No.: PCT/JP2015/084939
§ 371 (c)(1),
(2) Date: Oct. 10, 2017

(87) PCT Pub. No.: WO2016/166921
PCT Pub. Date: Oct. 20, 2016

(65) Prior Publication Data
US 2018/0072655 A1    Mar. 15, 2018

(30) Foreign Application Priority Data

Apr. 14, 2015  (JP) .................. 2015-082591

(51) Int. Cl.
| | |
|---|---|
| *C07D 209/48* | (2006.01) |
| *C07C 213/06* | (2006.01) |
| *C07C 217/90* | (2006.01) |
| *C08G 73/10* | (2006.01) |
| *G01R 33/46* | (2006.01) |

(52) U.S. Cl.
CPC .......... *C07C 213/06* (2013.01); *C07C 217/90* (2013.01); *C07D 209/48* (2013.01); *C08G 73/1078* (2013.01); *G01R 33/46* (2013.01)

(58) Field of Classification Search
CPC .................................................. C07D 209/48
See application file for complete search history.

(56) References Cited

U.S. PATENT DOCUMENTS

| | | |
|---|---|---|
| 5,567,800 A | 10/1996 | Hergenrother et al. |
| 6,281,323 B1 | 8/2001 | Yokota et al. |

FOREIGN PATENT DOCUMENTS

| | | |
|---|---|---|
| JP | 2000-219741 A | 8/2000 |
| JP | 2006-104440 A | 4/2006 |
| JP | 2011-1279 A | 1/2011 |

OTHER PUBLICATIONS

Chen et al., Journal of Membrane Science, available online Feb. 28, 2015, 483, pp. 144-154.*
Yokota. "Polyimide and Aromatic Polymer." Recent Progress, pp. 20-25, 2013.
"Recent Polyimide, Fundamentals and Applications." Japan Polyimide and Aromatic Polymer Conference, pp. 222-230.

* cited by examiner

*Primary Examiner* — Laura L. Stockton
(74) *Attorney, Agent, or Firm* — Oliff PLC

(57) ABSTRACT

An asymmetric diamine suitable for preparing a soluble polyimide and a method for preparing the same, including a compound represented by the following formula (1):

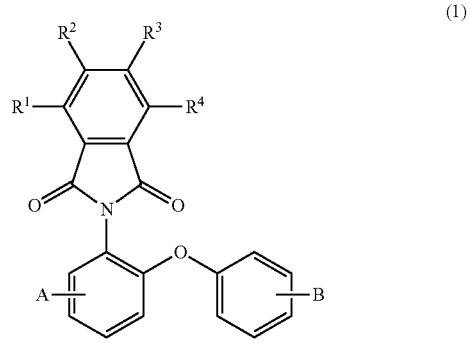

wherein $R^1$, $R^2$, $R^3$ and $R^4$ are, independently of each other, a hydrogen atom, an alkyl group having 1 to 6 carbon atoms, or an alkoxy group having 1 to 3 carbon atoms, and A and B are, independently of each other, a nitro group or an amino group. Further, a method for preparing the compound represented by the aforesaid formula (1).

6 Claims, 4 Drawing Sheets

AROMATIC DIAMINE, AN INTERMEDIATE THEREFOR, A METHOD FOR PRODUCING THE AROMATIC DIAMINE, AND A METHOD FOR PRODUCING THE INTERMEDIATE THEREFOR

FIELD OF THE INVENTION

The present invention relates to diamino-2-phthalimidodiphenyl ether, derivatives therefor and methods for preparing them. These compounds are useful as raw materials for highly functional polymers including polyimides, and various organic compounds. The present invention further relates to an intermediate for diamino-2-phthalimidodiphenyl ether, i.e., aminonitro-2-phthalimidodiphenyl ether, dinitro-2-phthalimidodiphenyl ether and derivatives from these, and methods for preparing them.

BACKGROUND OF THE INVENTION

Recently, polymer materials have been desired which have high heat resistance, high tenacity in extreme conditions such as in cosmic space, and easy moldability. Patent Literature 1 describes a method of attaining high heat resistance in molding without generating volatile components by heat curing while maintaining good processability wherein a polyimide oligomer is heated and capped with a capping agent such as phenylethynylphthalic anhydride, molded, heated and, then, crosslinked and cured at the phenylethynyl group. Patent Literature 2 discloses a method for improving flowability and processability of an oligomer using asymmetric tetracarboxylic anhydride in the preparation of a composite of carbon fiber and polyimide. A cardo-type diamine is used in Patent Literature 3. The asymmetric diamine disclosed in Patent Literature 4 is 2-(4-aminophenoxy)-5-aminobiphenyl.

In particular, 2-(4-aminophenoxy)-5-aminobiphenyl described in Patent Literature 4 is a raw material for preparing a polymer having high heat resistance, high tenacity and easy moldability and broadens the potentiality of asymmetric polyimides (Non-Patent Literature 1). Non-Patent Literature 2 describes that many of asymmetric polyimides have a high melt flowability on account of active segmental movement at a temperature higher than a glass-transition temperature. Therefore, further asymmetric diamines are desired to be used as a raw material of asymmetric polyimides.

PRIOR LITERATURES

Patent Literatures

[Patent Literature 1] U.S. Pat. No. 5,567,800
[Patent Literature 2] Japanese Patent Application Laid-Open No. 2000-219741
[Patent Literature 3] Japanese Patent Application Laid-Open No. 2006-104440
[Patent Literature 4] Japanese Patent Application Laid-Open No. 2011-1279

Non-Patent Literatures

[Non-patent Literature 1] Recent Polyimide, Fundamentals and Applications, edited by Japan Polyimide and Aromatic Polymer Conference, pages 222 to 230

[Non-Patent Literature 2] Polyimide and Aromatic Polymer, Recent Progress 2013, edited by Rikio Yokota, pages 20 to 25

SUMMARY OF THE INVENTION

Problems to be Solved by the Invention

Accordingly, one of the purposes of the present invention is to provide an asymmetric diamine suitable for preparing a soluble polyimide and a method for preparing the same.

To solve the aforesaid problems, the present inventors have made research and developed novel asymmetric diamines which are diamino-2-phthalimidodiphenyl ether, derivatives therefrom and intermediates for diamino-2-phthalimidodiphenyl ether, i.e., aminonitro-2-phthalimidodiphenyl ether, dinitro-2-phthalimidodiphenyl ether, and derivatives from these. The present inventors have further found that diamino-2-phthalimidodiphenyl ether and derivatives thereof have good properties comparable to the properties of 2-(4-aminophenoxy)-5-aminobiphenyl and that these compounds are easily prepared.

Thus, the present invention provides a compound represented by the following formula (1):

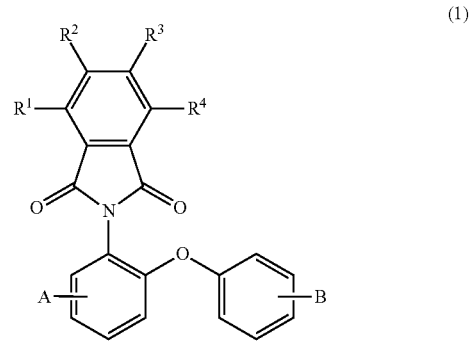

wherein $R^1$, $R^2$, $R^3$ and $R^4$ are, independently of each other, a hydrogen atom, an alkyl group having 1 to 6 carbon atoms, or an alkoxy group having 1 to 3 carbon atoms, and A and B are, independently of each other, a nitro group or an amino group.

The present invention further provides a method for preparing the compound represented by the aforesaid formula (1).

Effects of the Invention

Diamino-2-phthalimidodiphenyl ether and its derivatives can be suitably used as an asymmetric diamine, broaden the potentiality of the field of polyimides derived from the compounds and provide new functional materials.

DETAILED DESCRIPTION OF THE INVENTION

The Present Compound

Figure 1:
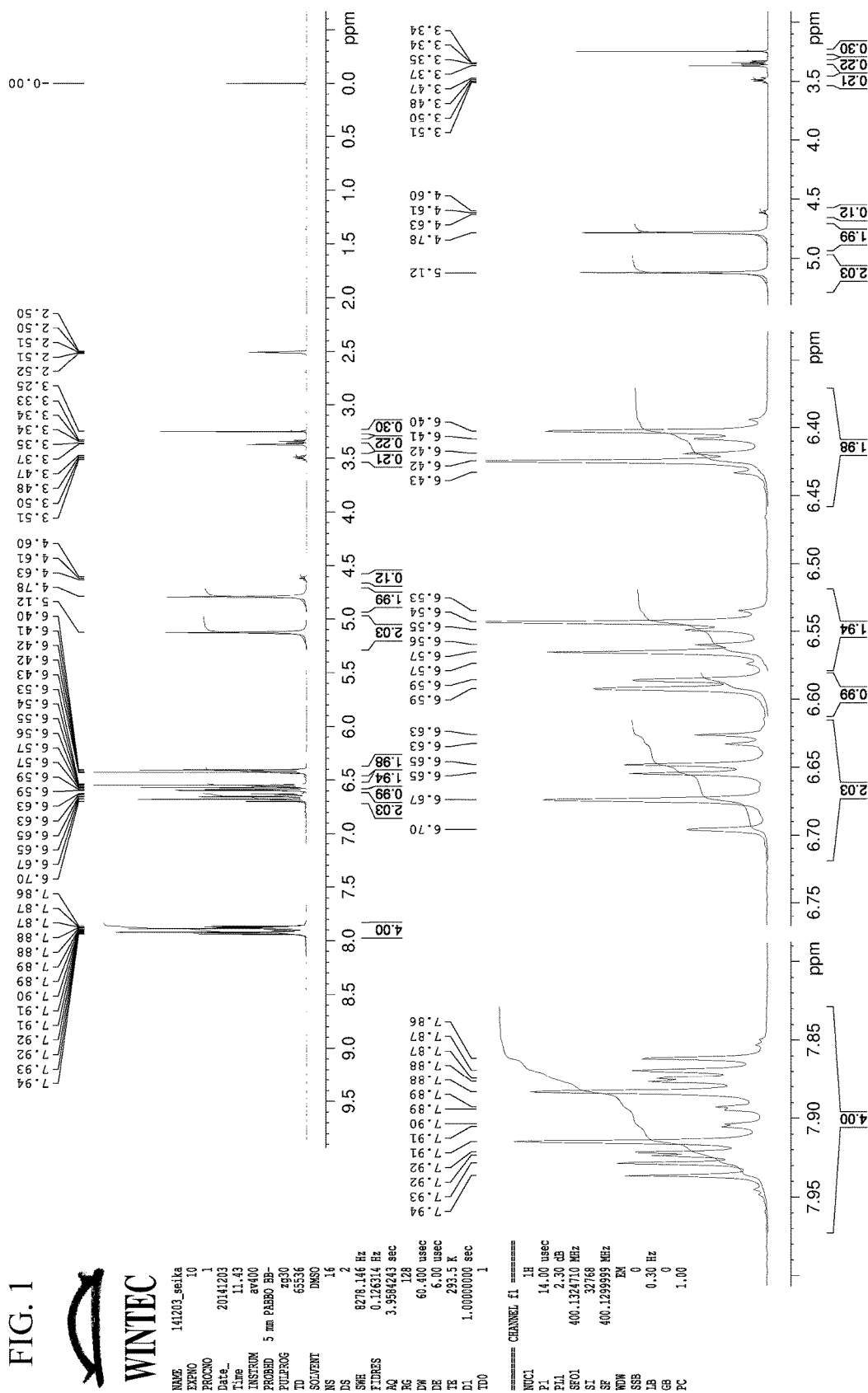
FIG. 1 is a chart of $^1$H-NMR spectra of the compound prepared in Example 2.

The present compound is a phthalimidodiphenyl ether which has an amino group and/or a nitro group or its derivatives and is represented by the following formula (1).

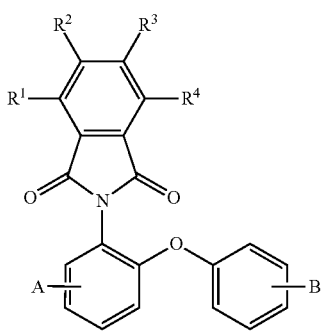

(1)

wherein $R^1$, $R^2$, $R^3$ and $R^4$ are, independently of each other, a hydrogen atom, an alkyl group having 1 to 6 carbon atoms, or an alkoxy group having 1 to 3 carbon atoms, and A and B are, independently of each other, a nitro group or an amino group.

In the aforesaid formula (1), A is bonded to one of the carbon atoms at position 3, 4, 5 or 6 in the benzene ring. B is bonded to one of the carbon atoms at position 2', 3' or 4' in the benzene ring. The positions in the benzene ring are illustrated below. Preferred is that A and B are both an amino group or A and B are both a nitro group, in particular A and B are both an amino group.

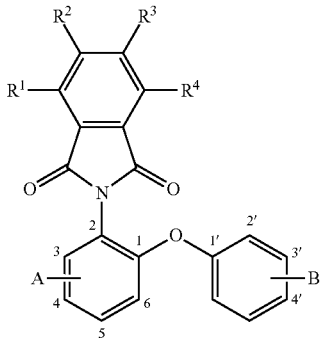

In the formula (1), the alkyl group having 1 to 6 carbon atoms may be branched. Examples of the alkyl group include a methyl group, an ethyl group, a propyl group, an isopropyl group, a butyl group, a pentyl group, and a hexyl group. Among these, an alkyl group having 1 to 3 carbon atoms is preferable. Examples of the alkoxy group having 1 to 3 carbon atoms include a methoxy group, an ethoxy group, a propoxy group, and an isopropoxy group. In particular, $R^1$, $R^2$, $R^3$ and $R^4$ are, independently of each other, a hydrogen atom or an alkyl group having 1 to 3 carbon atoms, further preferably a hydrogen atom.

The compound whose A and B in the formula (1) are both an amino group is represented by the formula (1-a) and is diamino-2-phthalimidodiphenyl ether or its derivatives.

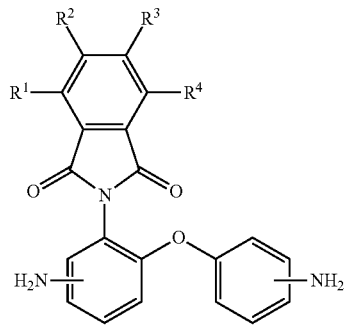

(1-a)

wherein $R^1$, $R^2$, $R^3$ and $R^4$ are as defined above.

The compound represented by the formula (1-a) is preferably one represented by the following formula.

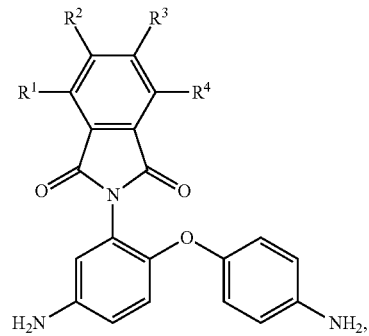

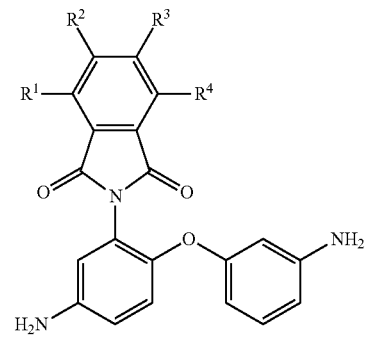

wherein $R^1$, $R^2$, $R^3$ and $R^4$ are as defined above, preferably are a hydrogen atom or an alkyl group having 1 to 3 carbon atom, further a hydrogen atom.

The compound whose A and B in the formula (1) are both an nitro group is represented by the following formula (1-b) and is dinitro-2-phthalimidodiphenyl ether and its derivatives. This compound may be used as an intermediate for the aforesaid diamino-2-phthalimidodiphenyl ether or its derivatives, which are represented by the formula (1-a).

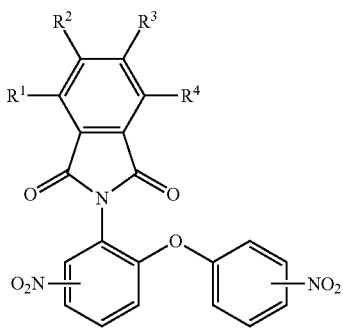

(1-b)

wherein $R^1$, $R^2$, $R^3$ and $R^4$ are as defined above.

The compound whose one of A and B in the formula (1) is an amino group and the other is an nitro group is represented by the following formula (1-c) or (1-d) and is aminonitro-2-phthalimidodiphenyl ether or its derivatives. This compound may be used as an intermediate for the aforesaid diamino-2-phthalimidodiphenyl ether or its derivatives, which are represented by the formula (1-a).

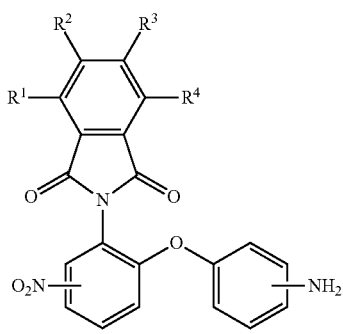

(1-c)

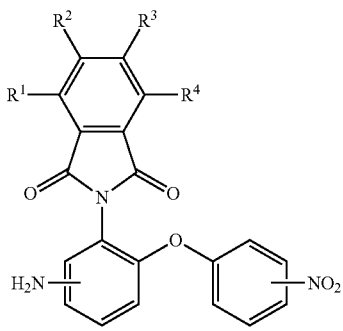

(1-d)

wherein $R^1$, $R^2$, $R^3$ and $R^4$ are as defined above.

[Preparation Method]

The compound represented by the formula (1-a) is obtained by reducing a nitro group(s) of the compound represented by the formula (1-b), (1-c) or (1-d). The compounds represented by the formula (1-b), (1-c) or (1-d) are prepared by the preparation method which will be explained below. The method of preparing the compound represented by the formula (1-a) may include a step for preparing the compound represented by the formula (1-b), (1-c) or (1-d) before the step of reduction. In particular, the compound represented by the formula (1-a) is preferably prepared by reducing the nitro groups of the compound represented by the formula (1-b).

The reduction reaction may be catalytic hydrogeneration reduction, bechamp reduction, reduction with zinc powder, reduction with tin chloride and reduction with hydrazine. Catalytic hydrogeneration reduction is preferred.

Examples of a solvent used in the reduction reaction include alcohols such as methanol, ethanol, 1-propanol, isopropanol, 1-butanol, 2-methoxyethanol and 2-ethoxyethanol; amides such as N,N-dimethylformamide, N,N-dimethylacetamide, N-methylpyrrolidone and N,N'-dimethylimidazolidinone; and ethers such as tetrahydrofuran, dioxane, ethylene glycol dimethyl ether, and diethylene glycol. The amount of the solvent may be properly adjusted.

Any known catalyst for reduction reactions may be used. For instance, examples of the catalyst used in the catalytic hydrogeneration reduction include novel metal catalysts such as palladium, platinum or rhodium supported on activated carbon, carbon black, graphite or alumina; raney nickel catalyst; and sponge nickel catalyst. The amount of the catalyst is generally 0.1 to 10 wt %, but is not limited.

A reaction temperature and a period of time of the reduction reaction may be properly selected. For instance, the reaction may be conducted at 50 to 150 degrees C., preferably 60 to 100 degrees C., for 1 to 10 hours, preferably 3 to 5 hours. After end of the reaction, for instance, the catalyst is removed, the reaction solution is cooled, and a resulting solid is filtrated off, washed with water and dried to thereby obtain the compound represented by the formula (1-a).

The compound represented by the aforesaid formula (1-b) is obtained by reacting a compound represented by the following formula (2), 2-amino-dinitrodiphenyl ether:

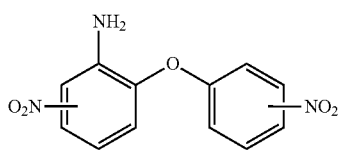

(2)

with a compound represented by the following formula (3), (3') or (3"),

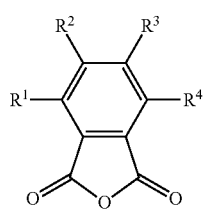

(3)

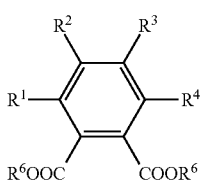

(3')

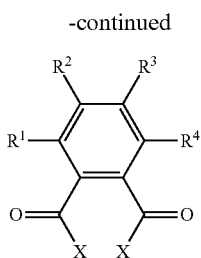

wherein $R^1$, $R^2$, $R^3$ and $R^4$ are as defined above, $R^6$ is a hydrogen atom, or an alkyl group having 1 to 4 carbon atoms such as a methyl group and an ethyl group, and X is a halogen atom such as a chlorine atom and a bromine atom (i.e., imidization).

The compound represented by the aforesaid formula (2) is obtained by reacting a 2-amino-nitrophenol salt represented by the following formula (a1) with a halogenated nitrobenzene compound represented by the following formula (b1) (i.e., etherification),

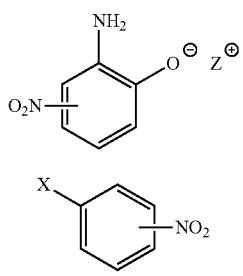

wherein Z is an alkali metal or an alkali earth metal and X is a halogen atom.

Alternatively, the compound represented by the aforesaid formula (2) is obtained by reacting a halogenated nitrobenzene amine (or nitroaniline) compound represented by the following formula (a2) with a nitrophenol compound represented by the following formula (b2) or a metal salt of said nitrophenol compound (i.e., etherification),

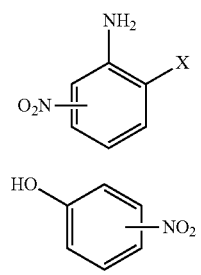

wherein X is a halogen atom.

Examples of the halogen atom include a chlorine atom, a fluorine atom, a bromine atom, and an iodine atom.

Examples of the 2-amino-nitrophenol salt represented by formula (a1) include a 2-amino-3-nitrophenol lithium salt, a 2-amino-3-nitrophenol sodium salt, a 2-amino-3-nitrophenol potassium salt, a 2-amino-3-nitrophenol magnesium salt, a 2-amino-3-nitrophenol calcium salt, a 2-amino-4-nitrophenol lithium salt, a 2-amino-4-nitrophenol sodium salt, a 2-amino-4-nitrophenol potassium salt, a 2-amino-4-nitrophenol magnesium salt, a 2-amino-4-nitrophenol calcium salt, a 2-amino-5-nitrophenol lithium salt, a 2-amino-5-nitrophenol sodium salt, a 2-amino-5-nitrophenol potassium salt, 2-amino-5-nitrophenol magnesium salt, a 2-amino-5-nitrophenol calcium salts, a 2-amino-6-nitrophenol lithium salt, a 2-amino-6-nitrophenol sodium salt, a 2-amino-6-nitrophenol potassium salt, a 2-amino-6-nitrophenol magnesium salt and 2-amino-6-nitrophenol calcium salts. These salt may be prepared in a reaction mixture by adding hydroxide, carbonate or bicarbonate of an alkali metal or an alkali earth metal corresponding to the 2-amino-nitrophenol compounds.

Examples of the halogenated nitrobenzene represented by the aforesaid formula (b1) include 2-fluoro-nitrobenzene, 3-fluoro-nitrobenzene, 4-fluoro-nitrobenzene, 2-chloro-nitrobenzene, 3-chloro-nitrobenzene, 4-chloro-1-nitrobenzene, 2-bromo-nitrobenzene, 3-bromo-nitrobenzene, 4-bromo-nitrobenzene, 2-iodo-nitrobenzene, 3-iodo-nitrobenzene and 4-iodo-nitrobenzene.

Examples of the halogenated nitrobenzene amine (or nitroaniline) represented by the aforesaid formula (a2) include 2-chloro-4-nitroaniline, 2-fluoro-4-nitroaniline, 2-bromo-4-nitroaniline, 2-chloro-5-nitroaniline, 2-fluoro-5-nitroaniline, and 2-bromo-5-nitroaniline.

Examples of the nitrophenol compound represented by the aforesaid formula (b2) or a metal salt of said phenol compound include 2-nitrophenol, 3-nitrophenol, 4-nitrophenol, a 2-nitrophenol sodium salt, a 3-nitrophenol sodium salt, a 4-nitrophenol sodium salt, a 2-nitrophenol potassium salt, a 3-nitrophenol potassium salt, a 4-nitrophenol potassium salt, a 2-nitrophenol calcium salt, a 3-nitrophenol calcium salt, and a 4-nitrophenol calcium salts.

Examples of the phthalic anhydride represented by the aforesaid formula (3) include unsubstituted phthalic anhydride, 3-methyl phthalic anhydride, 4-methyl phthalic anhydride, 3-ethyl phthalic anhydride, 4-ethyl phthalic anhydride, 3-propyl phthalic anhydride, 4-propyl phthalic anhydride, 3-isopropyl phthalic anhydride, 4-isopropyl phthalic anhydride, 3,4-dimethyl phthalic anhydride, 3,4-diethyl phthalic anhydride, 3,4-dipropyl phthalic anhydride and 3,4-diisopropyl phthalic anhydride. The phthalic acid compound represented by the aforesaid formula (3') is a phthalic acid corresponding to the aforesaid phthalic anhydride compounds or phthalic esters such as dimethyl phthalate and diethyl phthalate. The phthalic acid compound represented by the aforesaid formula (3") may be phthalic chloride.

In the etherification, amounts of the raw compounds are such that a mole ratio of the halogenated nitrobenzene represented by the formula (b1) to the 2-amino-nitrophenol salt represented by the formula (a1) is preferably 1.0 to 1.5, further preferably 1.05 to 1.2. In the imidization, amounts of the raw compounds are such that a mole ratio of the phthalic anhydride or the phthalic acid compound to the 2-amino-dinitrodiphenyl ether represented by the formula (2) is preferably 1.0 to 2.0, further preferably 1.0 to 1.2.

The compound represented by the formula (1-c) is obtained by reacting 2-amino-nitrophenol salt represented by the formula (a1) with the phthalic anhydride or a phthalic acid compound to prepare a compound represented by the following formula (a') (i.e., imidization) and, then, reacting the compound (a') with a halogenated aminobenzene compound represented by the following formula (c) (i.e., etherification).

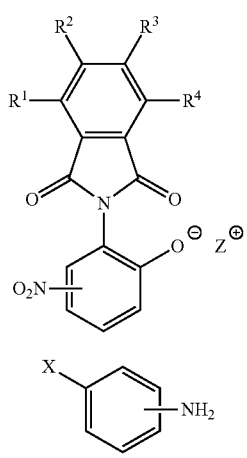
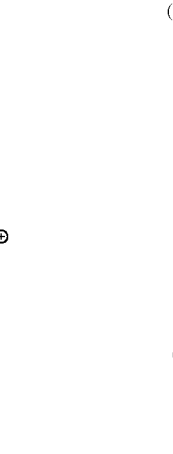

wherein X is a halogen atom.

Examples of the halogenated aminobenzene represented by the aforesaid formula (c) include 2-fluoro-aminobenzene, 3-fluoro-aminobenzene, 4-fluoro-aminobenzene, 2-chloro-aminobenzene, 3-chloro-aminobenzene, 4-chloro-amino benzene, 2-bromo-aminobenzene, 3-bromo-aminobenzene, 4-bromo-aminobenzene, 2-iodo-aminobenzene, 3-iodo-aminobenzene, and 4-iodo-aminobenzene.

The compound represented by the aforesaid formula (1-d) is obtained by reacting an amino-2-phthalimidophenol salt which is represented by the following formula (d) and obtained by reducing a nitro group of the compound (a') with the halogenated nitrobenzene compound represented by the aforesaid formula (b1) (i.e., etherification).

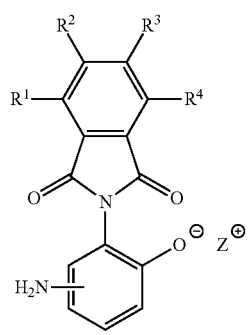

The reduction reaction of the nitro group of the compound (a') may be catalytic hydrogenation reduction, bechamp reduction, reduction with zinc powder, reduction with tin chloride and reduction with hydrazine. Catalytic hydrogeneration reduction is preferred. The solvent, the catalyst and the reaction conditions which are described for the method of preparing component (1-a) may be used in this reduction reaction.

The etherification and the imidization may be conducted in the presence of a solvent. The kinds and the amount of the solvent may be selected properly as in known manners. For instance, an aprotic polar solvent may be used. Examples of the aprotic polar solvent include dimethylformamide, dimethylacetamide, N-methylpyrrolidone, N,N'-dimethylimidazolidinone, dimethylsulfoxide, sulfolane and hexamethylphosphoric triamide.

In the imidization, the formed water is preferably removed via azeotropy with toluene, xylene or n-hexane.

The imidization may be conducted in the presence of an acid catalyst. Any acid catalyst known as a catalyst for imidization may be used, such as sulfuric acid, phosphoric acid, p-toluenesulfonic acid, trifluoromethanesulfonic acid and methanesulfonic acid.

A reaction temperature and a period of time of the etherification and the imidization may be selected properly as in known manners. For instance, the etherification may be carried out at 25 to 250 degrees C., preferably 50 to 200 degrees C., for 1 to 24 hours, preferably 5 to 12 hours. The imidization may be carried out at 100 to 200 degrees C., preferably 120 to 160 degrees C., for 2 to 20 hours, preferably 5 to 10 hours. After-treatment of a resulting product is not limited.

EXAMPLES

The present invention will be explained below in further detail with reference to a series of the Examples and the Comparative Examples, though the present invention is in no way limited by these Examples.

In the following descriptions, the HPLC determination was conducted by SPD-10A, ex Shimadzu Corporation, and the melting point was determined by MP-21, ex Yamato Scientific Co., Ltd.

Synthesis Example 1

Synthesis of 2-amino-4,4'-dinitrodiphenyl ether

To a one-liter, four-neck flask equipped with a stirrer and a thermometer, 88.0 g of 2-amino-4-nitrophenol sodium salt, 53.6 g of 4-fluoronitrobenzene, 11.0 g of potassium carbonate and 400 g of N,N-dimethylacetamide were added and allowed to react at 60 degrees C. for 20 hours and further at 80 degrees C. for 8 hours. Then, 400 g of ion-exchanged water was added dropwise. A resulting solid was filtered off, washed with water and then dried to obtain 85.7 g of 2-amino-4,4'-dinitrodiphenyl ether. A purity determined by HPLC was 99.7% and a melting point was 170 to 171 degrees C.

Example 1

Synthesis of 4,4'-dinitro-2-phthalimidodiphenyl ether

To a two-liter, four-neck flask equipped with a thermometer, a cooling tube, a Dean-Stark apparatus and a stirrer, 50.0 g of 2-amino-4,4'-dinitrodiphenyl ether, 28.7 g of phthalic anhydride, 500 g of N-methylpyrrolidone, 400 g of xylene, and 12.0 g of 98% sulfuric acid were added and allowed to react at 155 degrees C. for 5 hours while removing formed water via azeotropy with xylene. Then, the remaining xylene was removed at a reduced pressure, and the remaining solution was blown into 1500 g of an aqueous 75% isopropanol solution. A resulting solid was filtered off, washed with water, filtered off and then dried to obtain 68.4 g of a crude product, 4,4'-dinitro-2-phthalimidodiphenyl ether. A purity determined by HPLC was 98.6% and a melting point was 130 to 135 degrees C. 68.0 Grams of the crude product was dissolved in 200 g of N-methylpyrrolidone containing 6.8 g of activated carbon. The activated carbon was removed via filtration, and the filtrate was added to 600 g of an aqueous 75% isopropanol solution. A resulting solid was filtered off, washed with water, filtered off and then dried to obtain 61.2 g of purified 4,4'-dinitro-2-phthalimidodiphenyl ether. A purity determined by HPLC was 99.6% and a melting point was 132 to 134 degrees C.

Example 2

Synthesis of 4,4'-diamino-2-phthalimidodiphenyl ether

To a 300-milliliter of an autoclave, 10.0 g of 4,4'-dinitro-2-phthalimidodiphenyl ether obtained in Example 1, 100 g of N,N-dimethylformamide and 0.5 g of 5% Pd/C were added and subjected to catalytic hydrogenation reduction at 0.6 MPa at 75 to 80 degrees C. The catalyst was removed from the reaction solution. The reaction solution was concentrated, to which water was added to obtain 7.7 g of a solid product. A purity determined by HPLC was 99.5% and a melting point was 244 to 246 degrees C.

The product obtained was subjected to (i) $^1$H nuclear magnetic resonance spectrum analysis, (ii) $^{13}$C nuclear magnetic resonance spectrum analysis and (iii) mass analysis.

The $^1$H-NMR spectra was obtained with AVANCE400, ex Bruker Biospin, with a resonance frequency of 400 MHz. The solvent was dimethylsulfoxide-d6.

The $^{13}$C-NMR spectra was obtained with JNM-ECA600, ex JEOL Ltd., with a resonance frequency of 600 MHz. The solvent was dimethylsulfoxide-d6.

Mass analysis was carried out with AXIMA Confidence, ex Shimadzu Corporation.

According to the following results, the solid product obtained was identified as 4,4'-diamino-2-phthalimidodiphenyl ether.

(i) The $^1$H-NMR spectra were as described below. A chart of $^1$H-NMR spectra is shown in FIG. 1.

A singlet of a proton of an amino group was confirmed at delta 4.8 ppm (2H) and 5.1 ppm (2H); a doublet of a proton of the benzene nucleus was confirmed at delta 6.4 ppm (2H) and 6.6 ppm (2H); a doublet, a quartet, and a doublet of a proton of the benzene nucleus bonded to the phthalimide group were confirmed at delta 6.5 ppm (1H), 6.6 ppm (1H) and 6.7 ppm (1H); and a multiplet of a proton of the benzene nucleus of the phthalimide group was confirmed at delta 7.9 ppm (2H) and 8.0 ppm (21).

Figure 2:
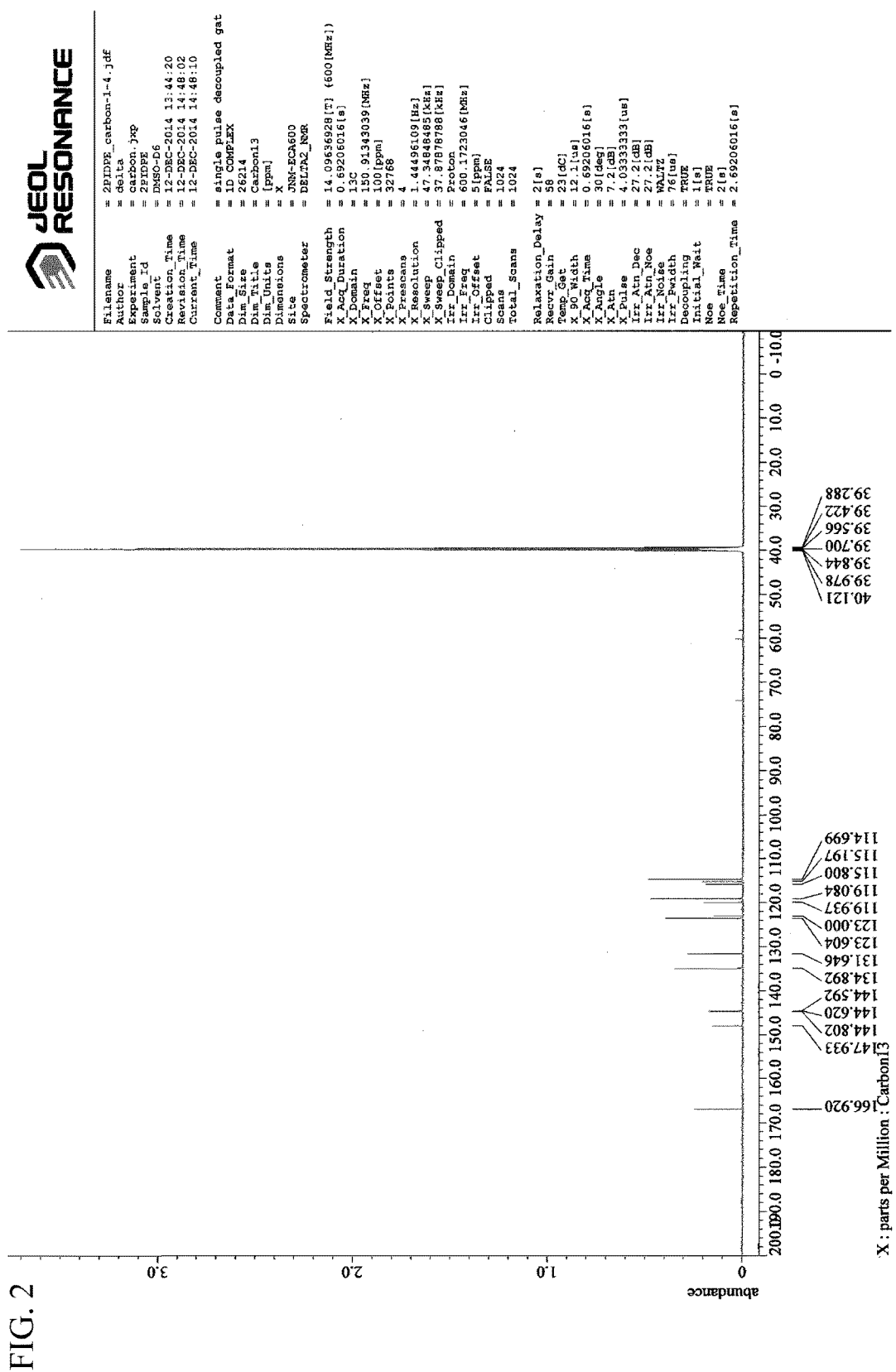
FIG. 2 is a chart of $^{13}$C-NMR spectra of the compound prepared in Example 2.

(ii) $^{13}$C nuclear magnetic resonance spectrum analysis showed 14 peaks. A chart of $^{13}$C-NMR spectra is shown in FIG. 2.

(iii) Mass analysis showed a main peak at 345.

Synthesis Example 2

Synthesis of 2-amino-3,4'-dinitrodiphenyl ether

To a 200-milliliter, four-neck flask equipped with a stirrer and a thermometer, 10.0 g of 2-fluoro-5-nitroaniline, 9.8 g of 3-nitrophenol, 4.9 g of potassium carbonate and 100 g of N,N-dimethylacetamide were added and allowed to react at 130 degrees C. for 5 hours. Then, 70 g of ion-exchanged water was added dropwise. A resulting solid was filtered off, washed with water and then dried to obtain 14.6 g of 2-amino-3,4'-dinitrodiphenyl ether. A purity determined by HPLC was 99.6% and a melting point was 175 to 176 degrees C.

Example 3

Synthesis of 3,4'-dinitro-2-phthalimidodiphenyl ether

To a 200-milliliter, four-neck flask equipped with a thermometer, a cooling tube, a Dean-Stark apparatus and a stirrer, 5.0 g of 2-amino-3,4'-dinitrodiphenyl ether, 2.9 g of phthalic anhydride, 50 g of N-methylpyrrolidone, 40 g of xylene, and 1.2 g of 98% sulfuric acid were added and allowed to react at 155 degrees C. for 2 hours while removing formed water via azeotropy with xylene. Then, xylene was removed at a reduced pressure, and the remaining solution was blown into 150 g of an aqueous 75% isopropanol solution. A resulting solid was filtered off, washed with water, filtered off and then dried to obtain 6.9 g of a crude product, 3,4'-dinitro-2-phthalimidodiphenyl ether. 6.5 Grams of the crude product was dissolved in 40 q of N-methylpyrrolidone containing an 0.7 g of activated carbon. The activated carbon was removed via filtration, and the filtrate was added to 150 g of an aqueous 75% isopropanol solution. A resulting solid was filtered off, washed with water, filtered off and then dried to obtain 6.1 g of purified 3,4'-dinitro-2-phthalimidodiphenyl ether. A purity determined by HPLC was 99.5% and a melting point was 163 to 164 degrees C.

Example 4

Synthesis of 3,4'-diamino-2-phthalimidodiphenyl ether

The process of Examples 3 was repeated.

To a 300-milliliter autoclave, 10.0 g of the resulting 3,4'-dinitro-2-phthalimidodiphenyl ether, 100 g of N,N-dimethylformamide and 0.5 g of 5% Pd/C were added and subjected to catalytic hydrogenation reduction at 0.6 MPa at 75 to 80 degrees C. The catalyst was removed from the reaction solution. The reaction solution was concentrated, to which water was added to obtain a 6.9 g of a solid product. A purity determined by HPLC was 98.2% and a melting point was 200 to 203 degrees C.

The product obtained was subjected to (i) $^1$H nuclear magnetic resonance spectrum analysis, (ii) $^{13}$C nuclear magnetic resonance spectrum analysis and (iii) mass analysis.

The $^1$H-NMR spectra and the $^{13}$C-NMR spectra were obtained with AVANCE400, ex Bruker Biospin, with a resonance frequency of 400 MHz. The solvent was dimethylsulfoxide-d6.

Mass analysis was carried out with LCMS-2020, ex Shimadzu Corporation.

According to the following results, the solid product obtained was identified as 3,4'-diamino-2-phthalimidodiphenyl ether.

Figure 3:
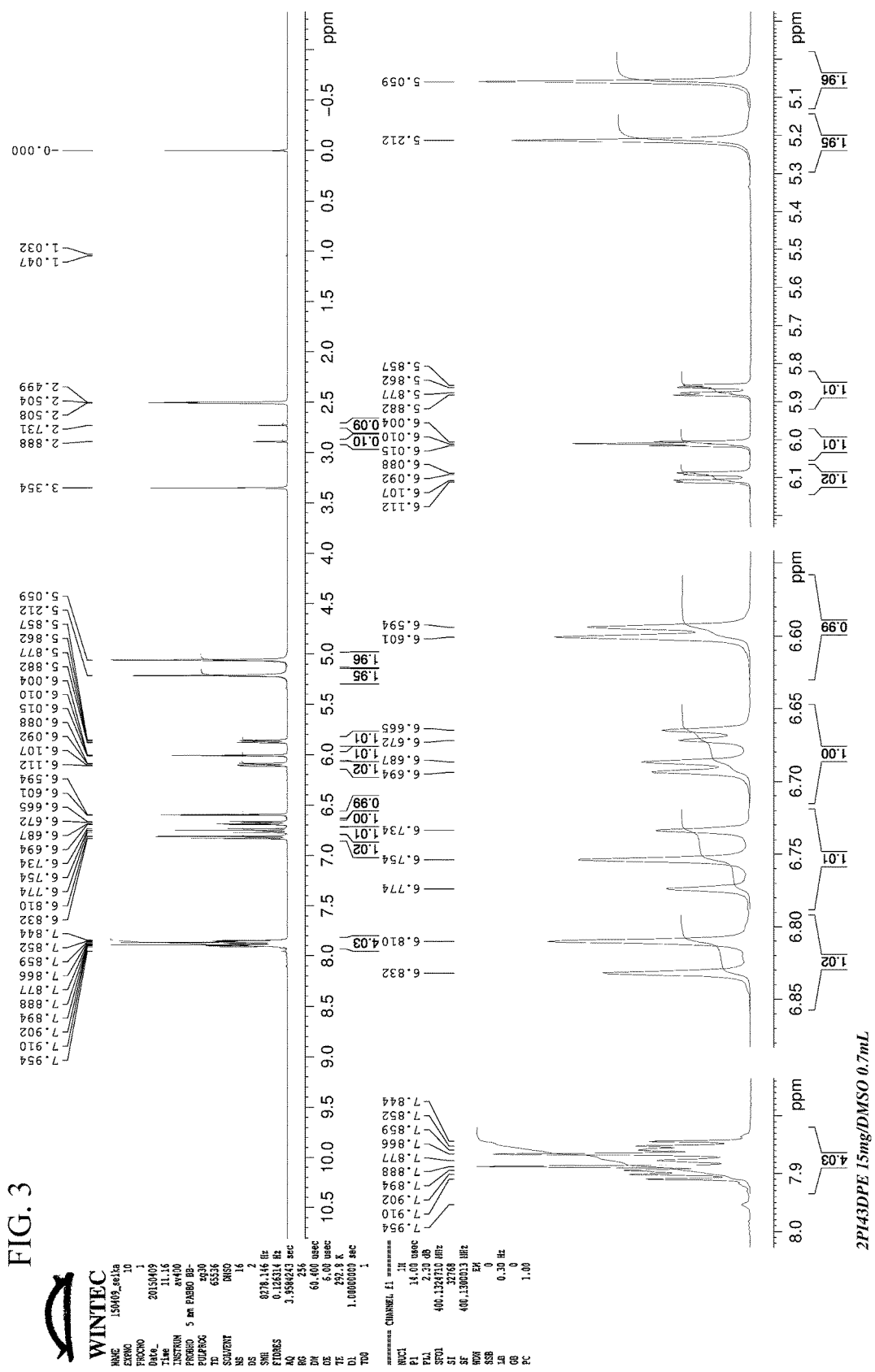
FIG. 3 is a chart of $^1$H-NMR spectra of the compound prepared in Example 4.

(i) The 1H-NMR spectra were as described below. A chart of $^1$H-NMR spectra is shown in FIG. 3.

A singlet of a proton of an amino group was confirmed at delta 5.1 ppm (2H) and 5.2 ppm (2H); a quartet, a triplet, a quartet, and a triplet of a proton of the benzene nucleus were confirmed at delta 5.9 ppm (1H), 6.0 ppm (1H), 6.1 ppm (1H) and 6.7 ppm (1H); a doublet, a quartet, and a doublet of a proton of the benzene nucleus bonded to the phthalimide group were confirmed at delta 6.6 ppm (1H), 6.7 ppm (1H) and 6.8 ppm (1H); and a multiplet of a proton of the benzene nucleus of the phthalimide group was confirmed at delta 7.8 to 8.0 ppm (4H).

Figure 4:
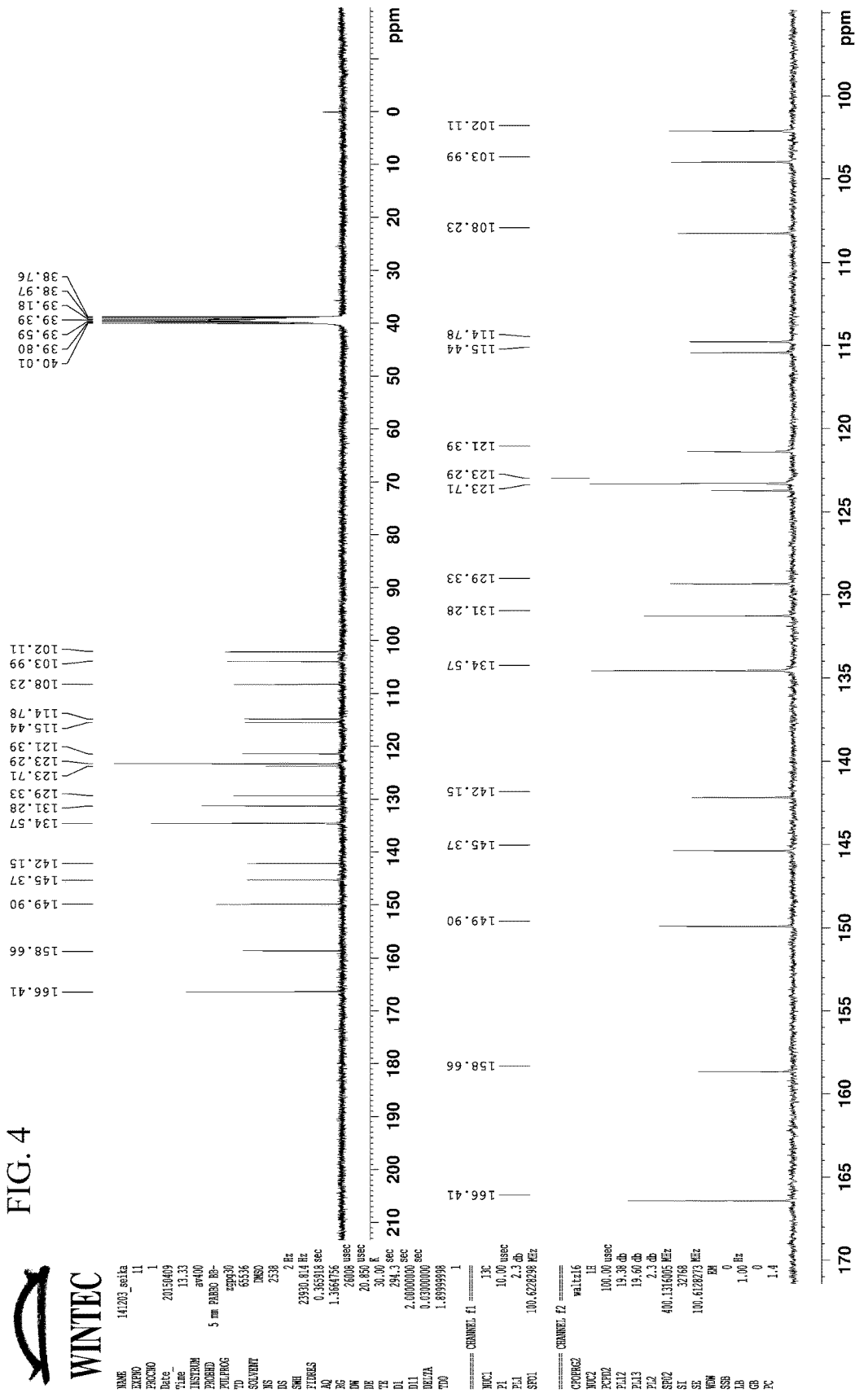
FIG. 4 is a chart of $^{13}$C-NMR spectra of the compound prepared in Example 4.

(ii) $^{13}$C nuclear magnetic resonance spectrum analysis showed 16 peaks. A chart of $^{13}$C-NMR spectra is shown in FIG. 4.

(iii) LCMS mass analysis with a positive ion showed a main peak at 346.

INDUSTRIAL APPLICABILITY

Diamino-2-phthalimidodiphenyl ether and its derivatives are suitably used as an asymmetric diamine, broaden the potentiality of the field of polyimides derived from the compounds and provide new functional materials. Dinitro-2-phthalimidodiphenyl ether, aminonitro-2-phthalimidodiphenyl ether and derivatives thereof are usable as an intermediate for diamino-2-phthalimidodiphenyl ether and derivatives thereof. These intermediates also broaden the potentiality of the field of polyimides.

The invention claimed is:

1. A compound represented by the following formula (1):

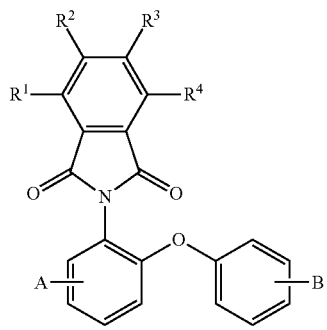

(1)

wherein $R^1$, $R^2$, $R^3$ and $R^4$ are, independently of each other, a hydrogen atom, an alkyl group having 1 to 6 carbon atoms, or an alkoxy group having 1 to 3 carbon atoms, and A and B are, independently of each other, a nitro group or an amino group.

2. The compound according to claim 1, wherein A and B are both an amino group.

3. A method for preparing a compound represented by the following formula (1-a):

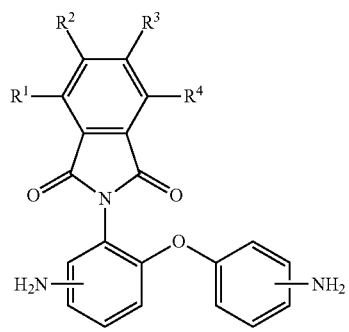

(1-a)

wherein $R^1$, $R^2$, $R^3$ and $R^4$ are, independently of each other, a hydrogen atom, an alkyl group having 1 to 6 carbon atoms, or an alkoxy group having 1 to 3 carbon atoms, wherein the method comprises a step of reducing a nitro group(s) of a compound represented by the following formula (1-b), (1-c) or (1-d) to thereby prepare the compound represented by the aforesaid formula (1-a),

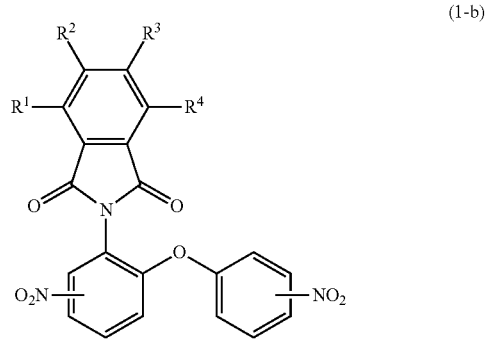

(1-b)

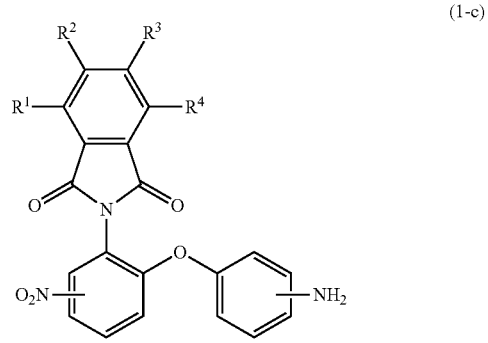

(1-c)

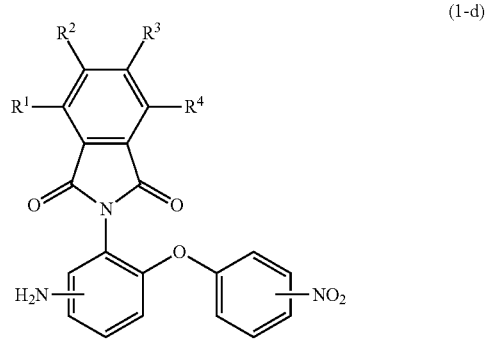

(1-d)

wherein $R^1$, $R^2$, $R^3$ and $R^4$ are as defined above.

4. A method for preparing a compound represented by the following formula (1-b):

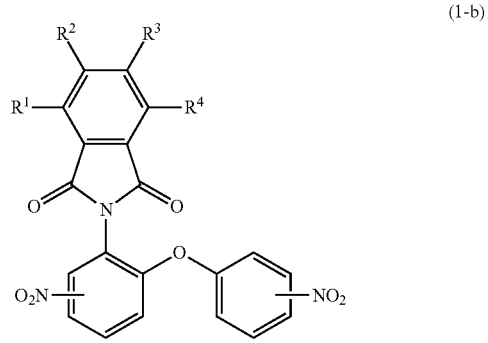

(1-b)

wherein R¹, R², R³ and R⁴ are, independently of each other, a hydrogen atom, an alkyl group having 1 to 6 carbon atoms, or an alkoxy group having 1 to 3 carbon atoms, wherein the method comprises a step of reacting a compound represented by the following formula (2):

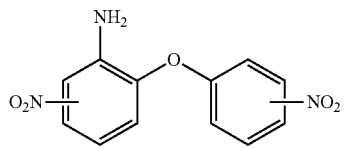
(2)

with a compound represented by the following formula (3), (3') or (3"):

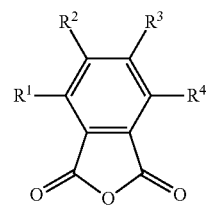
(3)

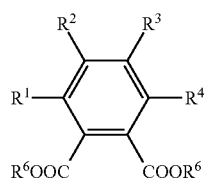
(3')

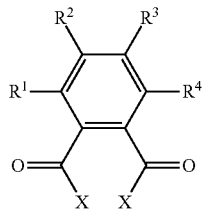
(3")

wherein R¹, R², R³ and R⁴ are as defined above, R⁶ is a hydrogen atom, or an alkyl group having 1 to 4 carbon atoms, and X is a halogen atom, to thereby prepare the compound represented by the aforesaid formula (1-b).

5. The method according to claim 4, wherein the method further comprises a step of reacting a 2-amino-nitrophenol salt represented by the following formula (a1):

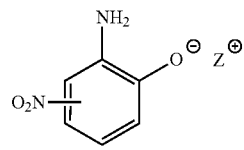
(a1)

wherein Z is an alkali metal or an alkali earth metal, with halogenated nitrobenzene represented by the following formula (b1):

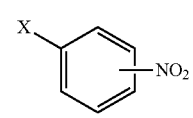
(b1)

wherein X is a halogen atom, to thereby prepare the compound represented by the aforesaid formula (2).

6. The method according to claim 4, wherein the method further comprises a step of reacting halogenated nitrobenzene amine represented by the following formula (a2):

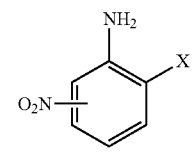
(a2)

wherein X is a halogen atom, with nitrophenol represented by the following formula (b2) or a metal salt of said nitrophenol

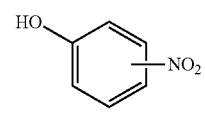
(b2)

to thereby prepare the compound represented by the aforesaid formula (2).

* * * * *